United States Patent [19]

Satoh et al.

[11] Patent Number: 5,109,025

[45] Date of Patent: Apr. 28, 1992

[54] THERAPEUTIC AGENT FOR PENAL DISORDERS

[75] Inventors: Toshio Satoh; Hitoshi Matsumoto; Hisao Kakegawa, all of Tokushima, Japan

[73] Assignees: Dainippon Ink and Chemicals, Inc.; Nippon Hypox Laboratories Incorporated, both of Tokyo, Japan

[21] Appl. No.: 543,845

[22] PCT Filed: Nov. 24, 1989

[86] PCT No.: PCT/JP89/01197

§ 371 Date: Jul. 25, 1990

§ 102(e) Date: Jul. 25, 1990

[87] PCT Pub. No.: WO90/06108

PCT Pub. Date: Jun. 14, 1990

[30] Foreign Application Priority Data

Nov. 25, 1988 [JP] Japan .................. 63-297847

[51] Int. Cl.$^5$ ............................................. A61K 31/12
[52] U.S. Cl. ....................................................... 514/679
[58] Field of Search ............................................ 514/679

[56] References Cited

U.S. PATENT DOCUMENTS

| | | | |
|---|---|---|---|
| 4,649,157 | 5/1987 | Partic et al. | 514/545 |
| 4,898,890 | 2/1990 | Sato et al. | 514/685 |
| 4,952,564 | 8/1990 | Sato et al. | 514/685 |

FOREIGN PATENT DOCUMENTS

| | | | |
|---|---|---|---|
| 0270690 | 6/1988 | European Pat. Off. | |
| 488485 | 3/1973 | Japan . | |
| 52-83937 | 7/1977 | Japan . | |
| 085278 | 2/1979 | Japan | 514/679 |
| 085279 | 2/1979 | Japan | 514/679 |
| 087809 | 2/1979 | Japan | 514/679 |
| 61-60609 | 3/1986 | Japan . | |
| 61-100547 | 5/1986 | Japan . | |
| 63-2925 | 1/1988 | Japan . | |
| 63-10720 | 1/1988 | Japan . | |
| 23816 | 2/1988 | Japan . | |

OTHER PUBLICATIONS

Komazawa et al., 1989, Chem. Abs. 110(3): "Antiulcer agents containing chalcone derivatives ..."–refering to JP Applicn. with date of Dec. 12, 1986.

Oganesyan et al., 1986 Chem. Abs. 105(15): 126832c, "Study of Structure Activity (SA) Interelations ...".

Yokumoto et al., 1989, Chem. Abs. 110(11):88620a. "Allergy inhibitors containing chalcone derivatives,–referring to patent document with date of Jul. 1, 1986".

Bhat et al., 1972, Indian J. Chem. 10:694-698. "Chemotherapy of Fungus infections ...".

Derwent Patent Abstracts, No. 89-059210 & Chemical Abstracts. vol. 111, No. 23, 4th Dec. 1989, p. 564, abstract No. 214230j, Columbus Ohio, U.S.; & JP-A-01 13 019 (Tsumura & Co.) Jan. 17, 1989 *Abstract*.

Chemical Abstracts, vol. 100, No. 19, Abstract No. 154304x (Chem. Abstr. 100 (19): 154304x), 7 May 1984, Brown, S., et al., Xenobiotica, 13 (11), 669 (1983).

Primary Examiner—S. J. Friedman
Attorney, Agent, or Firm—Oblon, Spivak, McClelland, Maier & Neustadt

[57] ABSTRACT

2',3,4,4'-tetrahydroxychalcone and pharmacologically acceptable salts thereof are used as a therapeutic agent for treatment of renal disorders, and have activity for treatment of renal disorders and also for treatment of renal disorders accompanied by digestive disorders, and/or general inflammations, and/or allergic diseases.

5 Claims, 1 Drawing Sheet

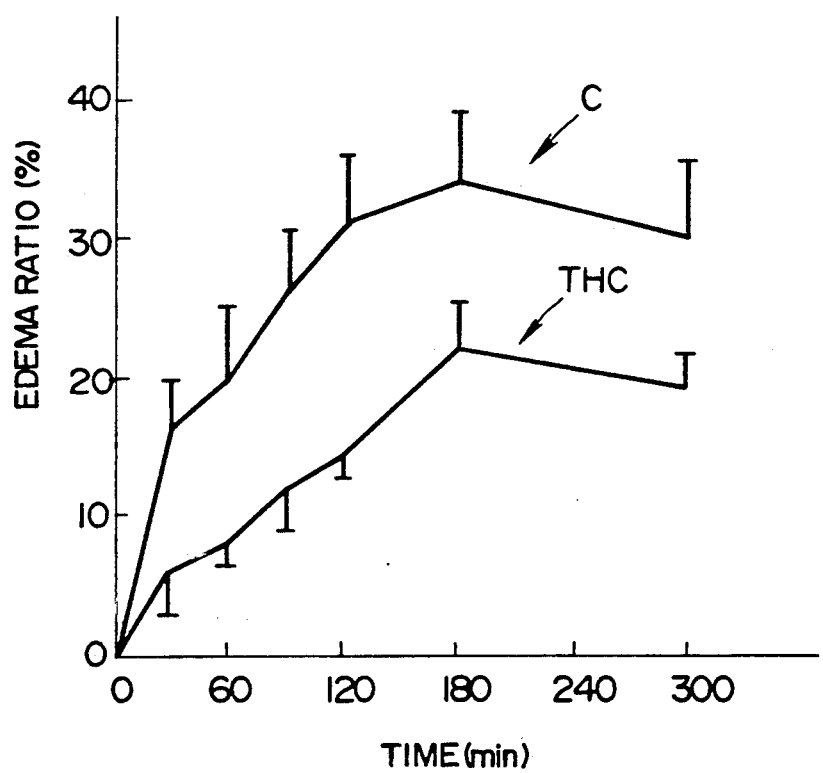
FIG.

THERAPEUTIC AGENT FOR RENAL DISORDERS

DESCRIPTION

1. Technical Field

The present invention relates to a therapeutic agent for renal disorders. More particularly, it relates to a therapeutic agent for renal disorders drug which has a therapeutical activity for the therapy of kidney disease, antiallergic activity and antiulcer activity as well as general antiinflammatory activity.

2. Background Art

Many nonsteroidal antiinflammatory drugs (NSAID) have heretofore been developed and they have been used widely for clinical therapy of various inflammatory diseases. However, these NSAID have a defect that they tend to cause serious side effects such as gastric ulcer and it is difficult to use them continuously for a long period of time although they exhibit potent antiinflammatory activity against acute inflammation. They have almost no effect against chronic inflammation and organ inflammation. For kidney diseases, there have heretofore been known few drugs inclusive of antiinflammatory drugs and diuretics and adrenocortical steroids have been used for the therapy of kidney diseases. However, they each exhibit poor therapeutical effect instead of high side effects. Thus, development of effective drugs has been desired.

The present inventors have previously found that isoliquiritigenin, one of chalcone derivatives, is effective as an antiallergic drug (Japanese Patent No. 1570239; Japanese Patent Application, Second Publication No. Hei 1-52363, Japanese Pat. No. 1570239, U.S. Pat. No. 4,952,564); and further that isoliquiritigenin is effective in the therapy and prophylaxis of kidney and liver diseases and proposed their use (Japanese Patent Application, First Publication No. Hei 1-104010) U.S. Pat. No. 4,898,890.

Furthermore, it has become clear in recent years that the chalcone derivative 2', 3, 4, 4'-tetrahydroxychalcone, also known as butein, which has a chemical structure resembling that of isoliquiritigenin, has antiallergy activity (Japanese Patent Application, First Publication Serial No. Sho-63-10720), antiulcer activity (Japanese Patent Application, First Publication Serial No. Sho. 63-150241, Japanese Patent Application, First Publication Serial No. Sho 64-42422), as well as general antiinflammatory activity (U.S. Pat. No. 4,279,930). However, no therapeutic activity against renal disorders has previously been demonstrated for this compound.

DISCLOSURE OF INVENTION

The present inventors have made intensive investigation with view to developing a novel therapeutic agent for renal disorders which has a therapeutical effect for kidney diseases more potent than isoliquiritigenin and which has also general antiinflammatory activity and antiallergic activity but does not cause injury to digestive organs and is of low toxicity. As the result, it has now been found that 2',3,4,4'-tetrahydroxychalcone (hereafter, sometimes referred to as "THC"), which is also called as "butein", and its salts have a therapeutical effect for kidney diseases more potent than isoliquiritigenin, have also general antiinflammatory activity and antiallergic activity, do not cause injury to digestive organs, and have in addition antiulcer activity, thus serving as a desirable drug for clinical therapy. The present invention has been completed based on this discovery.

Therefore, the present invention provides a therapeutic agent for renal disorders comprising as active ingredient 2',3,4,4'-tetrahydroxychalcone represented by formula (I)

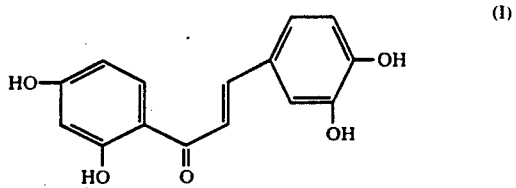

or its pharmacologically acceptable salt.

Furthermore, the present invention provides a method for the therapy of kidney diseases comprising administering to warm blooded animal a therapeutically effective amount for the therapy of the objective disease or diseases of a therapeutic agent for renal disorders comprising as active ingredient 2',3,4,4'-tetrahydroxychalcone represented by formula (I)

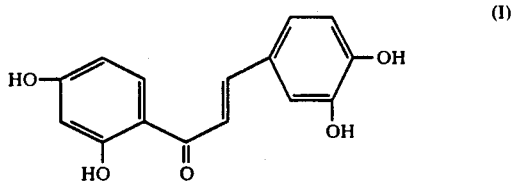

or its pharmacologically acceptable salt.

BRIEF DESCRIPTION OF DRAWINGS

Single figure is a graph representing the inhibitory activity of 2',3,4,4'-tetrahydroxychalcone against carragheenin plantar edema. In the figure, "THC" indicates a group administered with 2',3,4,4'-tetrahydroxy-chalcone and "C" a control group administered with a solvent.

BEST MODE FOR CARRYING OUT THE INVENTION

It is known that when conventional general antiinflammatory drugs are used in the therapy of kidney diseases, they in many cases aggravate kidney diseases contrary to expectation, and therefore general antiinflammatory drugs have almost no effect in the therapy of kidney diseases. The term "kidney diseases" used herein refers to (a) a functional disorder of the kidney which is caused by abnormality in the metabolic functions, for example, acute nephritis caused by drugs, etc., and chronic nephritis having developed from such acute nephritis, (b) acute nephritis caused by the intermediary of the immunological mechanism and chronic nephritis having developed from such acute nephritis, and (c) acute nephritis caused by bacterial or viral infection and chronic nephritis having developed from such acute nephritis, including a wide range of functional disorders of kidney sites such as the glomerulus, renal tubule and the lupus.

The pharmacologically acceptable salt of 2',3,4,4'-tetrahydroxychalcone includes non-toxic salts such as alkali metal salts and alkaline earth metal salts, e.g, sodium salt, potassium salt, magnesium salt, calcium salt, etc. as well as non-toxic amine salts, e.g., ammonium salt, and the like.

According to the present invention, 2',3,4,4' tetrahydroxychalcone and pharmacologically acceptable salts thereof are provided as a therapeutic agent for renal disorders, which in addition to the treatment of renal disease, are also exceedingly useful in the treatment of renal disorders accompanied by general inflammation, and/or digestive disorders, and/or allergic disease, and are also exceedingly useful in the treatment of acute inflammation in general, gastric ulcer disease, and allergic disease.

2',3,4,4'-tetrahydroxychalcone which can be used as the active ingredient of the therapeutic agent for renal disorders according to the present invention can be synthesized by a method analogous to known manufacturing method (D. R. Nadkarni, T., S. wheeler: *J. CHEM. SOC.*. 1320-1321 (1938)). This compound is also available commercially. The salts of the compound which are used as the active ingredient can readily be obtained from the compound in the conventional manner.

The therapeutic agent for renal disorders of the present invention can be administered by oral or parenteral administration (for example, venous injection, subcutaneous administration, rectal administration, etc.). Upon administration, it can be prepared in a suitable formulation depending on the method of administration.

The drug can be prepared in a formulation such as a tablet, a capsule, a granule, a powder, a fine granule, a pill, a troche, a buccal, a suppository, an ointment, an injection, an emulsion, a suspension, or a syrup, depending on the use. The preparation can be performed by known methods by using a non-toxic additive or additives that are usually employed in the preparation of drug of this kind, such as an excipient, a binder, a disintegrator, a lubricant, a preservative, an isotonizing agent, a stabilizer, a dispersing agent, an antioxidant, a colorant, a corrigent and a buffer. As for the non-toxic additives which can be used in the therapeutic agent for renal disorders of the present invention, there can be cited, for example, starch, gelatin, glucose, lactose, fructose, maltose, magnesium carbonate, talc, magnesium stearate, methylcellulose, carboxymethylcellulose, gum arabic, polyethylene glycol, propylene glycol, petrolatum, glycerol, ethanol, simple syrup, sodium chloride, sodium sulfite, sodium phosphate, citric acid, polyvinylpyrrolidone, water, and the like.

The drug of the present invention can also contain one or more other useful drugs.

The content of THC or its salt in the drug varies depending on the formulation. In general, it should preferably be contained in a concentration of from 0.1 to 100% by weight. The dosage of the drug of the present invention can be varied within a wide range in accordance with the kind of warm-blooded animal including humans to which it is administered, the seriousness of the disease, and the diagnosis by the doctor, but the dosage in terms of the active ingredient may range from 0.01 to 300 mg/kg/day/ However, these dosage ranges can be varied in accordance with the seriousness of the disease and the diagnosis by the doctor. Each of the above-mentioned dosages can be administered in a time or dividedly in several times a day.

EXAMPLES

The present invention will be described in detail wit reference to examples. However, it should no be construed that the present invention is limited thereto.

THC used in the examples is one synthesized from protocatechualdehyde and resacetophenone by a method analogous to the known synthesis method (J. CHEM. SOC., 1320-1321 (1938) referred to above).

EXAMPLE 1

Toxicity Tests

In this example, tests were conducted to confirm the safety of THC, which is the active ingredient of the drug of the present invention.

THC was administered by oral administration or intraperitoneal injection to five 5-week old male ddy mice. As the result, the minimum lethal dose was found to be not less than 3,000 mg/kg (oral administration) or not less than 1,000 mg/kg (intraperitoneal injection).

EXAMPLE 2

Antiinflammatory Activity

The antiinflammatory activity of THC was tested by using carragheenin-induced paw edema method widely used for the evaluation of the effectiveness of general antiinflammatory drugs (NSAID).

Test Method

A 1%-$\lambda$-carragheenin physiological saline solution (0.1 ml) was subcutaneously injected to the right paw of an SD male rat weighing from 200 to 250 g, and the volume of paw was measured after 30, 60, 90, 120, 180 and 300 minutes, respectively. The test drug (THC) had been administered orally in a dosage of 1.0 ml/200 g 60 minutes before the administration of carragheenin. The control group was administered orally with the solvent only in the same dosage. Edema ratio was calculated according to the following equation.

$$Edema\ Ratio = [(P_s - P_0)/P_0] \times 100$$

where Ps stands for value measured at a point in time after elapse of a predetermined time, and $P_0$ value indicates a value measured at 0 minute after the administration.

The results obtained are illustrated in the figure.

From the figure, it is apparent that THC exhibits marked inhibitory effect against carragheenin-induced edema in a dosage of 300 mg/kg, and thus confirming its effectiveness as antiinflammatory drug.

EXAMPLE 3

Activity for the Therapy of Kidney Diseases:
Cis-Platinum-Induced Kidney Injury Model Test In this example, tests were conducted to examine the therapeutical activity of THC against kidney injury induced by cis-platinum (cis-DDP) which is an anti-cancer drug and is known to have a very strong effect of inducing functional disorders of the kidney.

Test Method

A group of ten ddy male mice each weighing from 20 to 25 g were orally administered with 100 mg/kg/day of THC or isoliquiritigenin (positive comparative compound) for 5 continuous days, subcutaneously injected with 17 mg/kg of cis-platinum once on the fifth day, and were treated moreover for 5 continuous days orally administered with THC or isoliquiritigenin in the same manner as above. Thereafter, blood samples were collected, and blood urea nitrogen (BUN) in the serum was measured.

In the test, a group of ten non-treated ddy male mice each weighing from 20 to 25 g were subcutaneously administered once with 17 mg/kg of cis-platinum only. This group was used as control.

For the measurement of blood urea nitrogen, there was used Urea NB-Test Wako (produced by Wako Pure Chemical Industry Co., Ltd.). The results obtained are shown in Table 1.

TABLE 1

|  | Blood Urea Nitrogen |
|---|---|
| Non-treated group | 27.9 ± 2.6 |
| Cis-platinum | 114.7 ± 18.4 |
| Cis-platinum + THC | 47.1 ± 12.6** |
| Cis-platinum + isoliquiritigenin | 70.6 ± 14.0* |

Significant difference for cis-platinum-administered group
(**: $P < 0.01$, *: $P < 0.05$)

From the results shown in Table 1, it is apparent that THC suppressed the increase in blood urea nitrogen due to kidney injury induced by cis-platinum more potently than isoliquiritigenin, thus confirming effectiveness as a drug for the therapy of kidney diseases.

EXAMPLE 4

Antiulcer Activity: HCl-Ethanol Ulcer Model Test

Antiulcer activity was tested using hydrochloric acid-ethanol-induced ulcer model test which is widely used for evaluating the effectiveness of antiulcer drugs.

Test Method

A group of five SD male rats each weighing from 200 to 250 g were starved for 24 hours, and then administered orally with 1.0 ml/200 g of 150 mM hydrochloric acid-60% ethanol. After 1 hour, the animals were sacrificed with ether, and the stomach was taken out from each animal. After pouring 10 ml of physiological saline in each of them the stomachs were dipped in 1% formalin solution for 10 minutes to fix them. Each of the stomachs was incised along the greater curvature (curvatura ventriculi major) and the lengths of mucosal ulcers which appeared in the gastric gland portion were measured under microscope (×10). The sum of the lengths per animal was calculated and defined as ulcer index. Test drugs were administered orally in a dose of 1.0 ml/200 g after 10 minutes from the induction of stress. Cetraxate hydrochloride known as antiulcer drug was used as positive comparative compound. The results obtained are shown in Table 2 below.

TABLE 2

|  | Dose | Number of Animal | Ulcer Index | Inhibition Ratio |
|---|---|---|---|---|
| Control group (Ulcer-ocurring control group) | — | 5 | 46.7 ± 34.6 | — |
| THC | 100 | 5 | 1.2 ± 2.5** | 97.3 |
| Cetraxate hydrochloride | 100 | 5 | 11.2 ± 20.0** | 75.7 |

Significant difference for control group (**: $P < 0.01$)

From the results shown in Table 2, it is apparent that THC exhibited remarkable inhibitory activity against hydrochloric acid-ethanol-induced ulcer, thus confirming its effectiveness as antiulcer drug.

EXAMPLE 5

Antiallergic Activity: Test on Inhibition of Histamine Liberation from Mast Cells (1) Preparation of Rat Peritoneal Exudation Cells Locke's solution (10 ml) containing 0.1% by weight of bovine serum albumin was injected into the abdominal cavity of a rat which had been sacrificed by exsanguination. The rat was lightly massaged, then subjected to an abdominal section so that an abdominal solution was collected. The abdominal cavity was also washed with 5 ml of the same solution and the washing solution was collected and mixed with the above abdominal solution. The abdominal solution was centrifuged at 500 rpm for 5 minutes, then 5 ml of cool Locke's solution was added to the sediment. After the sediment had been washed, 3 ml of cool Locke's solution was again added thereto to form a solution of rat peritoneal exudation cells.

(2) Inhibition Effect of THC on Liberation of Histamine by Compound 48/80

Locke's solution (0.5 ml) and 1.0 ml of THC or isoliquiritigenin solution prepared in a concentration of 0.03 mM (THC or isoliquiritigenin was dissolved in a physiological saline solution containing 1% sodium bicarbonate, the resultant solution being diluted with Locke's solution) was added to 0.3 ml of the solution of rat peritoneal exudation cells obtained in (1) above and were incubated at 37° C. for 5 minutes. Then, 0.2 ml each of a Lock's solution of Compound 48/80 (1 mg/100 ml) was added to the solution and the mixture was incubated at 37° C. for 10 minutes. After the reaction was stopped by cooling, the obtained solution was centrifuged at 2,500 rpm for 10 minutes to separate into 1.7 ml of supernatant and 0.3 ml of sediment. Water (0.1 ml) and 0.2 ml of 100% trichloroacetic acid were added to the supernatant, and 1.5 ml of Locke's solution and the 100% trichloroacetic acid were added to the sediment which was then allowed to stand for 30 minutes at room temperature and was centrifuged at 3000 rpm for 15 minutes. A portion (0.35 ml) of each of the supernatant and the supernatant of the sediment was taken and 1.65 ml of water and 0.4 ml of 1N sodium hydroxide were added in turn to each of the supernatants. 0.5% OPT (orthophthalaldehyde) methanol solution (0.1 ml) was added to each of the resultant solutions which were then allowed to react at room temperature for 4 minutes. After the reaction was stopped by the addition of 0.2 ml of 2M citric acid, the fluorescence of each of the reaction solutions was measured by a fluorophotometer.

As a control, Locke's solution was added instead of the solution of THC and, as a blank, the Locke's solution was added instead of THC and Compound 48/80, the other operations being the same as those described above.

The inhibition ratio of THC or isoliquiritigenin for the liberation of histamine by Compound 48/80 is calculated from the following equations:

$$\text{Liberation Ratio of histamine (\%)} = \frac{Ps}{Ps + Pr} \times 100 = A$$

Ps: Amount of free histamines (in the supernatant)
Pr: Amount of remaining histamines (in the sediment)

Inhibition Ratio = $100 - \frac{I - B}{C - B} \times 100$

I: Value of A of THC or isoliquiritigenin
C: Value of A of the control
B: Value of A of the blank
The results are shown in Table 3.

TABLE 3

|  | Liberation Ratio of Histamine (%) | Inhibition Ratio (%) |
|---|---|---|
| Control | 82.4 | — |
| THC (0.03 mM) | 10.4 | 91.1 |
| Isoliquiritigenin (0.03 mM) | 71.2 | 14.2 |
| Blank | 3.4 | — |

From the results shown in Table 3, it is apparent that THC exhibits inhibition effect on the histamine liberation from rat mast cells caused by Compound 48/80 more potent than isoliquiritigenin, thus confirming its effectiveness as antiallergic drug.

Next, examples of formulations containing THC as active ingredient are described.

Example 6

| 5 mg Tablet | |
|---|---|
| THC | 5 mg |
| Lactose | 137 mg |
| Starch | 45 mg |
| Carboxymethylcellulose calcium salt | 10 mg |
| Talc | 2 mg |
| Magnesium stearate | 1 mg |
| | 200 mg/tablet |

Crystals of THC were ground, lactose and starch were added thereto, and they were mixed. Starch paste (10%) was added to the mixture, and they were agitated to obtain a granule. After the granule was dried, the grains were dressed to a grain size of about 850 μm. It was then mixed with talc and magnesium stearate, and the mixture was formulated into tablets.

Example 7

| 25 mg Tablet | |
|---|---|
| THC | 25 mg |
| Lactose | 120 mg |
| Starch | 42 mg |
| Carboxymethylcellulose calcium salt | 10 mg |
| Talc | 2 mg |
| Magnesium stearate | 1 mg |
| | 200 mg/tablet |

Crystals of THC were ground, lactose and starch were added thereto, and they were mixed. Starch paste (10%) was added to the mixture, and they were agitated to obtain a granule. After the granule was dried, the grains were dressed to a grain size of about 850 μm. It was then mixed with talc and magnesium stearate, and the mixture was formulated into tablets.

Example 8

| 20 mg Capsule | |
|---|---|
| THC | 20 mg |
| Lactose | 53 mg |
| Starch | 25 mg |
| Magnesium stearate | 2 mg |

Example 8-continued

| 20 mg Capsule | |
|---|---|
| | 100 mg/capsule |

Crystals of THC were well ground, and starch, lactose and magnesium stearate were added thereto. After they had been mixed adequately, the mixture was charged into a capsule.

Example 9

| Injectable Composition | |
|---|---|
| THC | 100 mg |
| Nikkol HCO60 | 500 mg |
| Sodium chloride | 90 mg |
| Distilled water for injection | 10 ml |
| | 690 mg/10 ml |

Formulation amounts of THC, Nikkol and sodium chloride were dissolved in distilled water for injection and the resulting solution was adjusted to pH 7.0. One (1) ml aliquot of the solution was charged into each ampule.

Industrial Applicability

According to the present invention, a therapeutic agent for renal disorders which in addition to renal disease, also has activity against general inflammation, gastric ulcer disease and allergic disease.

We claim:

1. A method for treatment of renal disorders comprising administering to a warm blooded animal a therapeutically effective amount of 2', 3, 4, 4'-tetrahydroxychalcone represented by formula (I)

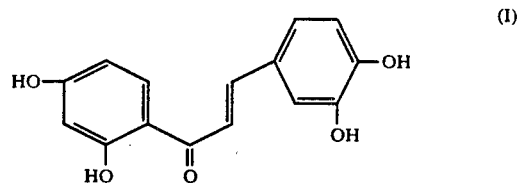

or its pharmacologically acceptable salt.

2. A method for treatment of renal disorders comprising administering to a warm blooded animal a therapeutically effective amount of 2', 3, 4, 4'-tetrahydroxychalcone represented by formula (I)

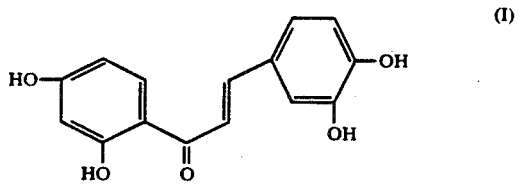

or its pharmacologically acceptable salt, administered by at least one of oral administration and parenteral administration.

3. A method for treatment of renal disorders comprising administering to a warm blooded animal a therapeutically effective amount of 2', 3, 4, 4'-tetrahydroxychalcone represented by formula (I)

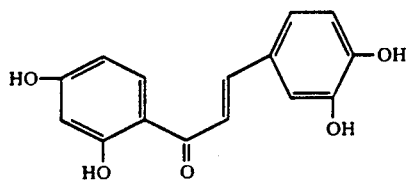

(I)

or its pharmacologically acceptable salt, administered parenterally by at least one of intravenous injection, subdermal injection and intraperitoneal injection.

4. The method of claim 1, wherein the administered tetrahydroxychalcone comprises a composition containing at least one non-toxic additive selected from the group consisting of an excipient, a binder, a disintegrator, a lubricant, a preservative, an isotonizing drug, a stabilizer, a dispersing drug, an antioxidant, a colorant, a corrigent and a buffer.

5. The method of claim 4, wherein the administered tetrahydroxychalcone composition contains 0.1 to 100% by weight of tetrahydroxychalcone.

* * * * *

UNITED STATES PATENT AND TRADEMARK OFFICE
CERTIFICATE OF CORRECTION

PATENT NO. : 5,109,025
DATED : April 28, 1992
INVENTOR(S) : Toshio Satoh et al.

It is certified that error appears in the above-identified patent and that said Letters Patent is hereby corrected as shown below:

Title page, item [54], and col. 1, line 1, should be, --THERAPEUTIC AGENT FOR RENAL DISORDERS--.

Signed and Sealed this

Thirteenth Day of July, 1993

Attest:

MICHAEL K. KIRK

Attesting Officer     Acting Commissioner of Patents and Trademarks